(12) United States Patent
Sato

(10) Patent No.: US 10,201,834 B2
(45) Date of Patent: Feb. 12, 2019

(54) ULTRASOUND OBSERVATION APPARATUS AND MANUFACTURING METHOD OF ULTRASOUND OBSERVATION APPARATUS

(71) Applicant: OLYMPUS CORPORATION, Tokyo (JP)

(72) Inventor: Sunao Sato, Yamato (JP)

(73) Assignee: OLYMPUS CORPORATION, Tokyo (JP)

( * ) Notice: Subject to any disclaimer, the term of this patent is extended or adjusted under 35 U.S.C. 154(b) by 179 days.

(21) Appl. No.: 15/426,161

(22) Filed: Feb. 7, 2017

(65) Prior Publication Data

US 2017/0144193 A1 May 25, 2017

Related U.S. Application Data

(63) Continuation of application No. PCT/JP2015/062255, filed on Apr. 22, 2015.

(30) Foreign Application Priority Data

Aug. 8, 2014 (JP) .................................. 2014-162807

(51) Int. Cl.
*B06B 1/06* (2006.01)
*A61B 8/12* (2006.01)
(Continued)

(52) U.S. Cl.
CPC .............. *B06B 1/0611* (2013.01); *A61B 8/12* (2013.01); *G01N 29/24* (2013.01); *H04R 17/00* (2013.01); *H04R 31/00* (2013.01)

(58) Field of Classification Search
CPC ....... B06B 1/0611; H04R 31/00; H04R 17/00; A61B 8/12; G01N 29/24
See application file for complete search history.

(56) References Cited

U.S. PATENT DOCUMENTS 4,220,887 A * 9/1980 Kompanek ......... H01L 41/0906
310/326
7,880,368 B2 * 2/2011 Sawada .................... A61B 8/12
310/322
(Continued)

FOREIGN PATENT DOCUMENTS

CN 106572841 A * 4/2017 ............... A61B 8/12
EP 1 918 027 A1 5/2008
(Continued)

OTHER PUBLICATIONS

International Search Report dated Aug. 4, 2015 issued in PCT/JP2015/062255.
(Continued)

*Primary Examiner* — Daniel Pihulic
(74) *Attorney, Agent, or Firm* — Scully, Scott, Murphy & Presser, P.C.

(57) ABSTRACT

An ultrasound observation apparatus includes: a sheet including a first transducer, a first transducer region, a columnar portion, and a film portion configured to connect a plurality of first upper electrodes in the first transducer region and a second surface of the columnar portion in an arrangement direction C; and a bonding portion provided between the first transducer positioned on a second end portion in the first transducer region and the columnar portion and configured to maintain a state in which the sheet is rounded such that the film portion becomes an external surface, and the first transducer positioned on the second end portion and a first surface of the columnar portion are attached to each other.

5 Claims, 6 Drawing Sheets

(51) Int. Cl.
*G01N 29/24* (2006.01)
*H04R 17/00* (2006.01)
*H04R 31/00* (2006.01)

(56) References Cited

U.S. PATENT DOCUMENTS

| | | | |
|---|---|---|---|
| 7,994,689 B2 * | 8/2011 | Sawada | A61B 8/12 310/327 |
| 2007/0293762 A1 | 12/2007 | Sawada et al. | |
| 2011/0140576 A1 * | 6/2011 | Sawada | A61B 8/12 310/334 |
| 2017/0144193 A1 * | 5/2017 | Sato | A61B 8/12 |
| 2017/0303893 A1 * | 10/2017 | Sato | A61B 8/12 |

FOREIGN PATENT DOCUMENTS

| | | | | |
|---|---|---|---|---|
| EP | 3165168 A1 * | 5/2017 | ............... | A61B 8/12 |
| EP | 3165168 A4 * | 4/2018 | ............... | A61B 8/12 |
| JP | H02-265533 A | 10/1990 | | |
| JP | H02-271839 A | 11/1990 | | |
| JP | 2006-094981 A | 4/2006 | | |
| JP | 2010-017229 A | 1/2010 | | |
| JP | 6072376 B2 * | 2/2017 | ............... | A61B 8/12 |
| JP | WO2016021244 A1 * | 4/2017 | ............... | A61B 8/12 |
| WO | WO 2006/033232 A1 | 3/2006 | | |
| WO | WO-2016021244 A1 * | 2/2016 | ............... | A61B 8/12 |

OTHER PUBLICATIONS

Extended Supplementary European Search Report dated Mar. 9, 2018 in European Patent Application No. 15 83 0708.2.

* cited by examiner

ULTRASOUND OBSERVATION APPARATUS AND MANUFACTURING METHOD OF ULTRASOUND OBSERVATION APPARATUS

CROSS REFERENCE TO RELATED APPLICATION

This application is a continuation application of PCT/JP2015/062255 filed on Apr. 22, 2015 and claims benefit of Japanese Application No. 2014-162807 filed in Japan on Aug. 8, 2014, the entire contents of which are incorporated herein by this reference.

BACKGROUND OF THE INVENTION

1. Field of the Invention

The present invention relates to an ultrasound observation apparatus and a manufacturing method of the ultrasound observation apparatus in which a plurality of ultrasound transducers including electrodes above and below a film portion are fixed on a sheet, and end portions of the sheet are bonded after the sheet is rounded.

2. Description of the Related Art

A well-known ultrasound observation apparatus exists in which ultrasound can be repeatedly emitted in a 360° direction from ultrasound transducers to an examined site, and the ultrasound transducers can receive an echo signal of the ultrasound reflected from the examined site. An ultrasound image that is a two-dimensional visible image of the examined site can be displayed on a screen of a display apparatus.

Japanese Patent Application Laid-Open Publication No. 2010-17229 discloses a configuration of an ultrasound endoscope provided with an ultrasound observation apparatus including electronic radial ultrasound transducers, the ultrasound observation apparatus provided on a distal end of an insertion portion inserted into a subject.

The electronic radial ultrasound transducers as disclosed in Japanese Patent Application Laid-Open Publication No. 2010-17229 are configured from a plurality of transducers. A plurality of electronic radial ultrasound transducers are arranged 360° in a circumferential direction of the insertion portion, at predetermined intervals.

More specifically, electrodes are usually provided on upper and lower surfaces of single-plate piezoelectric elements in the respective ultrasound transducers. Upper electrodes of the piezoelectric elements serving as acoustic emission surfaces are fixed to a film portion rounded 360°, at predetermined intervals in an arrangement direction of the plurality of ultrasound transducers.

Note that when an acoustic matching layer is provided on each upper electrode, each acoustic matching layer is fixed to the film portion rounded 360°, at predetermined intervals in the arrangement direction.

Therefore, the ultrasound observation apparatus includes a sheet in which the plurality of ultrasound transducers are fixed to the film portion rounded 360°, at predetermined intervals in the arrangement direction.

In the manufacture of the ultrasound observation apparatus described above, a joint of respective end portions of the sheet needs to be bonded and fixed such that the sheet on which at least a plurality of ultrasound transducers are fixed to the film portion has a circular shape after the sheet is rounded 360°.

In this case, in a transducer region of the sheet in which at least the plurality of ultrasound transducers are fixed to the film portion, the joint needs to be bonded and fixed to prevent electrical short-circuit caused by contact of a lower electrode of the ultrasound transducer fixed on a first end portion in the arrangement direction among the plurality of ultrasound transducers and a lower electrode of the ultrasound transducer adjacent to the ultrasound transducer fixed to the first end portion at the joint and fixed to a second end portion in the arrangement direction.

SUMMARY OF THE INVENTION

An aspect of the present invention provides an ultrasound observation apparatus including: a sheet including: a first transducer including a first upper electrode that is a GND electrode, a first piezoelectric element disposed on the first upper electrode, and a first lower electrode that is arranged in a predetermined arrangement direction on the first piezoelectric element and that is a positive electrode; a first transducer region in which the first transducer in plurality are arranged at predetermined intervals; a columnar portion in which at least a first surface is non-conductive, the columnar portion disposed adjacent to the first transducer positioned on a first end portion in the arrangement direction in the first transducer region; and a film portion that is flexible and that connects at least the first upper electrode in plurality in the first transducer region and a second surface facing the first surface of the columnar portion in the arrangement direction; and a bonding portion provided between the first transducer positioned on a second end portion in the arrangement direction among the first transducer in plurality in the first transducer region and the columnar portion and configured to maintain a state in which the sheet is rounded such that the film portion of the sheet becomes an external surface, and the first transducer positioned on the second end portion and the first surface of the columnar portion are attached to each other.

An aspect of the present invention provides a manufacturing method of an ultrasound observation apparatus, the manufacturing method including: a step of creating a sheet, the sheet including: a first transducer including a first upper electrode that is a GND electrode, a first piezoelectric element disposed on the first upper electrode, and a first lower electrode that is arranged on the first piezoelectric element and that is a positive electrode; a first transducer region in which the first transducer in plurality are arranged at predetermined intervals; a columnar portion in which at least a first surface is non-conductive, the columnar portion disposed adjacent to the first transducer positioned on a first end portion in an arrangement direction of the first transducer in plurality among the first transducer in plurality in the first transducer region; and a film portion that is flexible and that connects at least the first upper electrode in plurality in the first transducer region and a second surface facing the first surface of the columnar portion in the arrangement direction; a step of rounding the sheet such that the film portion of the sheet becomes an external surface, and the first transducer positioned on a second end portion in the arrangement direction among the first transducer in plurality in the first transducer region and the first surface of the columnar portion are attached to each other; and a step of maintaining, by a bonding portion, the state in which the sheet is rounded in the state in which the columnar portion and the first transducer positioned on the second end portion are attached to each other.

DETAILED DESCRIPTION OF THE PREFERRED EMBODIMENT(S)

Hereinafter, embodiments of the present invention will be described with reference to the drawings. Note that the drawings are schematic drawings, and a relationship between a thickness and a width of each member, a ratio of the thickness of respective members, and the like are different from the reality. It is obvious that the relationship and the ratio of dimensions between the drawings are different in some parts of the drawings.

First Embodiment

Figure 1:
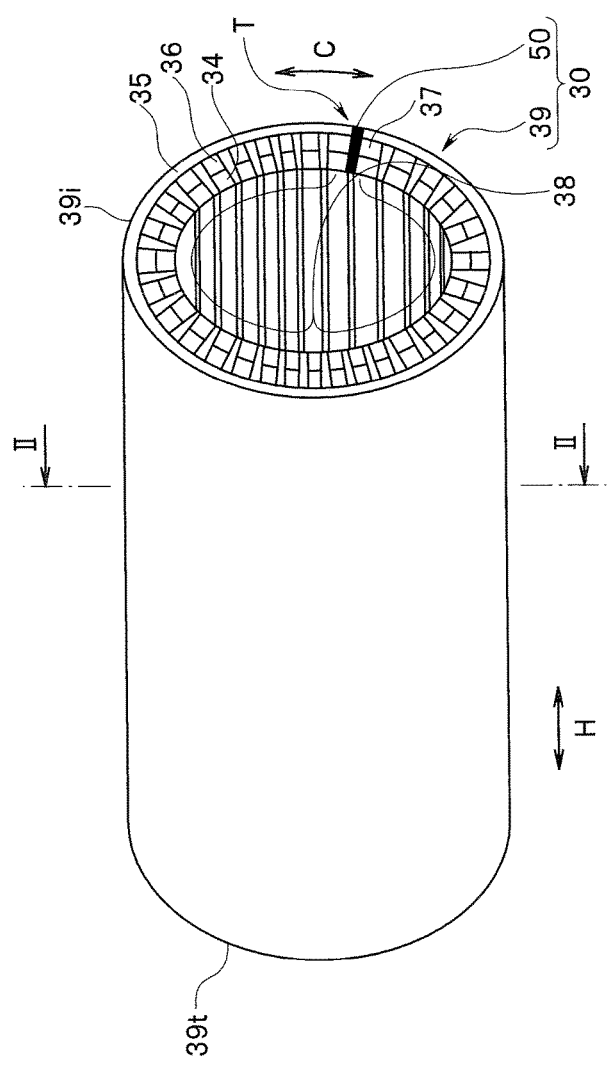
FIG. 1 is a perspective view schematically showing an ultrasound observation apparatus of a first embodiment.
Figure 2:
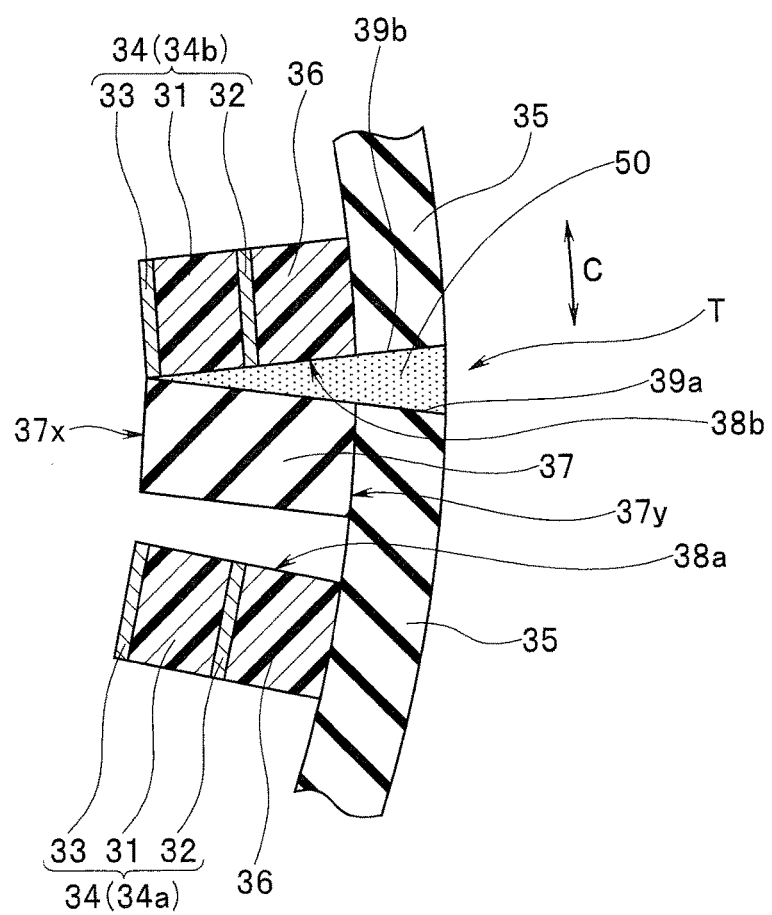
FIG. 2 is a partial cross-sectional view of the ultrasound observation apparatus along a line II-II in FIG. 1.

FIG. 1 is a perspective view schematically showing an ultrasound observation apparatus of the present embodiment. FIG. 2 is a partial cross-sectional view of the ultrasound observation apparatus along a line II-II in FIG. 1.

Figure 3:
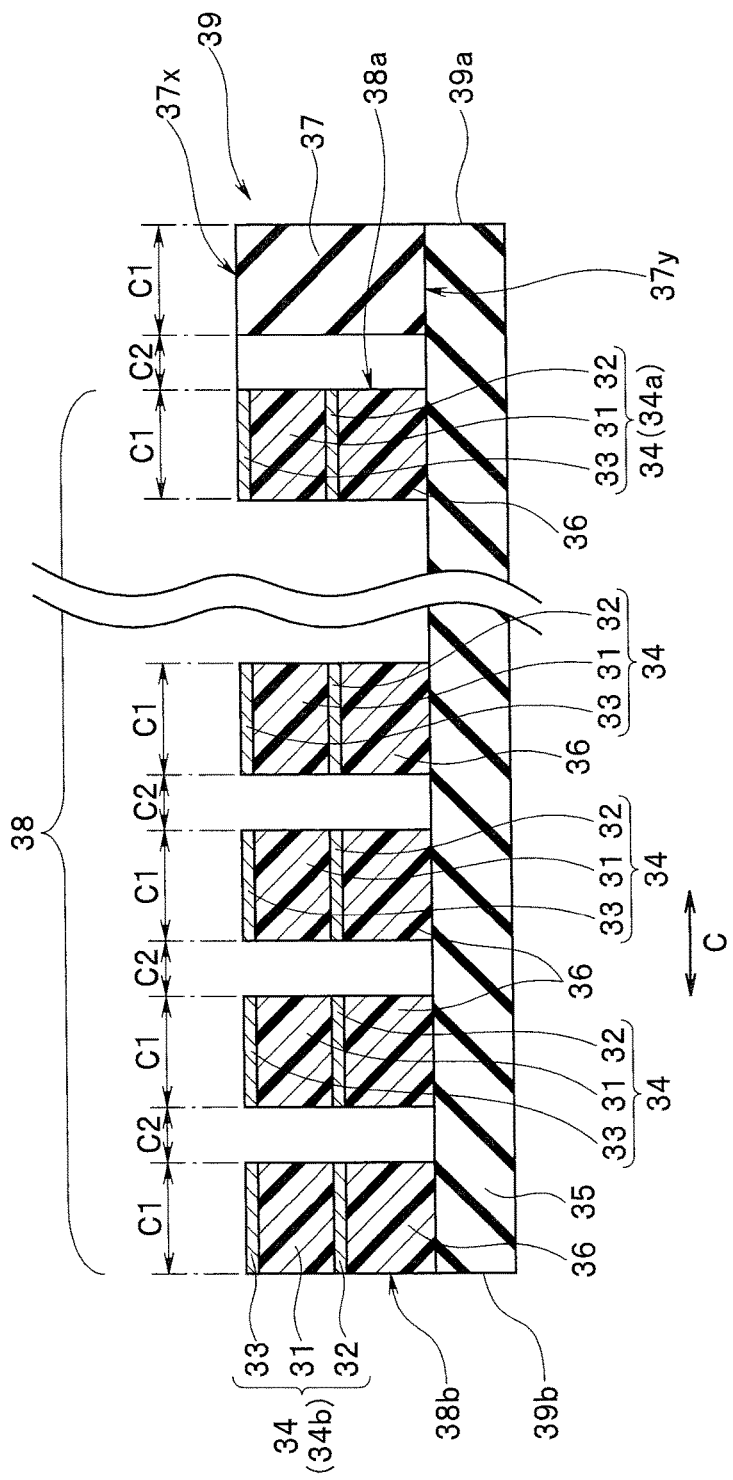
FIG. 3 is a cross-sectional view illustrated by removing a bonding portion from the ultrasound observation apparatus of FIG. 1 and developing a sheet.
Figure 4:
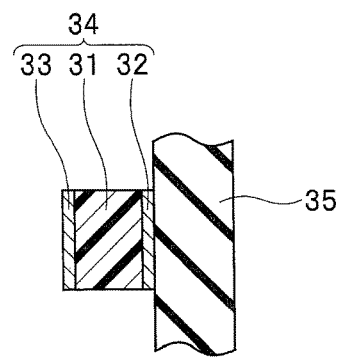
FIG. 4 is a partial cross-sectional view showing a modification in which a first upper electrode of a first ultrasound transducer of FIG. 1 is directly fixed to a film portion.

FIG. 3 is a cross-sectional view illustrated by removing a bonding portion from the ultrasound observation apparatus of FIG. 1 and developing a sheet. FIG. 4 is a partial cross-sectional view showing a modification in which a first upper electrode of a first ultrasound transducer of FIG. 1 is directly fixed to a film portion.

As shown in FIG. 1, an ultrasound observation apparatus 30 includes a sheet 39 and a bonding portion 50.

The sheet 39 is rounded 360° in an arrangement direction C described later and is elongated in an extension direction H.

More specifically, as shown in FIG. 3, main parts of the sheet 39 include a plurality of first transducers 34, a first transducer region 38, a columnar portion 37, an acoustic matching layer 36, and a film portion 35.

The plurality of first transducers 34 are electronic radial ultrasound transducers extending from one end 39$i$ to the other end 39$t$ in the extension direction H, each of the first transducers 34 including a first lower electrode 33, a first piezoelectric element 31 disposed on the first lower electrode 33, and a first upper electrode 32 disposed on the first piezoelectric element 31.

Each of the plurality of first transducers 34 has a width of C1 in the arrangement direction C and is arranged at a predetermined interval C2 in the arrangement direction C.

The first piezoelectric element 31 emits ultrasound toward the first upper electrode 32 along with vibration and receives a sound wave reflected from an examined site.

The first upper electrode 32 and the first lower electrode 33 are configured to apply a pulse voltage to the first piezoelectric element 31 to vibrate the first piezoelectric element 31. In addition, the first upper electrode 32 configures a GND electrode, and the first lower electrode 33 configures a positive electrode.

The first transducer region 38 is configured by arranging the plurality of first transducers 34 at the predetermined intervals C2 in the arrangement direction C.

Note that the smaller the predetermined intervals C2 are, the larger C1 can be. As a result, the sensitivity of each of the first transducers 34 improves.

At least a first surface 37$x$ of the columnar portion 37 is non-conductive. The columnar portion 37 is disposed, at the predetermined interval C2, adjacent to a first transducer 34$a$ positioned on a first end portion 38$a$ in the arrangement direction C among the plurality of first transducers 34 in the first transducer region 38.

The columnar portion 37 has a width of C1 in the arrangement direction C and extends from the one end 39$i$ to the other end 39$t$ in the extension direction H. Note that the columnar portion 37 may be individually provided only near the one end 39$i$ and the other end 39$t$ in the extension direction H.

The film portion 35 is flexible and connects, in the arrangement direction C, the plurality of first upper electrodes 32 in the first transducer region 38 and a second surface 37$y$ facing the first surface 37$x$ of the columnar portion 37. Note that the film portion 35 may function as an acoustic matching layer or an acoustic lens.

As shown in FIGS. 1 to 3, the present embodiment illustrates an example of a configuration in which the acoustic matching layer 36 is disposed between each of the first upper electrodes 32 and the film portion 35, that is, the present embodiment illustrates an example of a configuration in which each of the first upper electrodes 32 is connected by the second surface 37$y$ and the film portion 35 through each acoustic matching layer 36.

The arrangement is not limited to this, and as shown in FIG. 4, each of the first upper electrodes 32 may be directly fixed to the film portion 35 to connect each of the first upper electrodes 32 by the second surface 37$y$ and the film portion 35.

The bonding portion 50 bonds a joint T between respective end portions 39$a$ and 39$b$ in the arrangement direction C that is a space extending from the one end 39$i$ to the other end 39$t$ in the extension direction H in the sheet 39. The bonding portion 50 bonds the joint T from the one end 39$i$ to the other end 39$t$ of the sheet 39 in the extension direction H.

More specifically, in a state in which the sheet 39 is rounded such that the film portion 35 becomes an external surface as shown in FIG. 1, and a first transducer 34$b$ positioned on a second end portion 38$b$ and part of the non-conductive first surface 37$x$ of the columnar portion 37 are attached to each other as shown in FIG. 2, the bonding portion 50 is configured to bond, in the extension direction H, the columnar portion 37 and the first transducer 34$b$ at the joint T between the respective end portions 39$a$ and 39$b$ in the arrangement direction C of the sheet 39.

Note that the bonding portion 50 is configured from, for example, an adhesive. The bonding portion 50 may be configured from the same material as the film portion 35.

Next, a manufacturing method of the ultrasound observation apparatus 30 configured in this way will be simply described.

First, a step of creating the sheet 39 shown in FIG. 3 is executed. To create the sheet 39, the film portion 35 is formed first. Next, when the acoustic matching layer 36 is used on the film portion 35, the acoustic matching layer 36 is formed by excluding a part where the columnar portion 37 is to be formed.

Next, the first piezoelectric element 31 provided with the electrodes 32 and 33 on upper and lower surfaces is bonded on the acoustic matching layer 36 at the same width as the acoustic matching layer 36 in the arrangement direction C, and the columnar portion 37 with the width C1 in the arrangement direction C is bonded on the film portion 35.

Subsequently, a plurality of grooves with the width C2 in the arrangement direction C are formed on the electrodes 32 and 33, the first piezoelectric element 31, and the acoustic matching layer 36 by using a dicing blade with the blade width C2, for each width C1 in the arrangement direction C.

As a result, the plurality of first transducers 34 with the width C1 are arranged on the film portion 35 at the predetermined intervals C2 in the arrangement direction C through the acoustic matching layer 36, and the sheet 39 with the predetermined interval C2 between the first transducer 34a and the columnar portion 37 in the arrangement direction C is created.

Next, a step of rounding the sheet 39 360° is executed as shown in FIGS. 1 and 2 such that the film portion 35 becomes the external surface, and the first transducer 34b positioned on the second end portion 38b and part of the first surface 37x of the columnar portion 37 are attached to each other.

Lastly, in the state in which the sheet 39 is rounded, a step of bonding by the bonding portion 50 is executed by injecting the bonding portion 50 between the columnar portion 37 and the first transducer 34b in the arrangement direction C. As a result, the ultrasound observation apparatus 30 is manufactured.

In this way, the present embodiment has illustrated that the columnar portion 37 in which at least the first surface 37x is non-conductive is disposed adjacent to the first transducer 34a positioned on the first end portion 38a at the predetermined interval C2 in the arrangement direction C among the plurality of first transducers 34 in the first transducer region 38 in the sheet 39 of the ultrasound observation apparatus 30.

The present embodiment has also illustrated that the bonding portion 50 bonds, in the extension direction H, the columnar portion 37 and the first transducer 34b in the arrangement direction C at the joint T of the sheet 39 in the state in which the sheet 39 is rounded such that the film portion 35 becomes the external surface, and the first transducer 34b positioned on the second end portion 38b and part of the non-conductive first surface 37x of the columnar portion 37 are attached to each other.

According to this, part of the non-conductive first surface 37x of the columnar portion 37 is in contact with the lower electrode 33 of the first transducer 34b at the joint T of the sheet 39, and unlike in the conventional techniques, the lower electrode 33 of the first transducer 34a does not come into contact.

Therefore, the columnar portion 37 can surely prevent electrical short-circuit at the joint T of the first transducer 34b and the first transducer 34a without separately using the spacer or the like, and the manufacturing yield of the ultrasound observation apparatus 30 improves.

Note that this is particularly effective when the predetermined intervals C2 are reduced to improve the sensitivity of each of the first transducers 34.

In addition, part of the first surface 37x of the columnar portion 37 is attached to the first transducer 34b, and the bonding portion 50 injected to the joint T does not flow out toward the inner circumference of the sheet 39. Therefore, there is a possibility that operation of compensating the outflow of the adhesive does not have to be additionally performed.

Furthermore, an operator can perform the bonding operation of the joint T just by abutting part of the first surface 37x of the columnar portion 37 to the first transducer 34b and injecting the bonding portion 50 to the joint T. Therefore, the operator can easily adjust the position of the joint T, and the bonding operability improves.

As a result, the simple configuration and method can provide an ultrasound observation apparatus and a manufacturing method of the ultrasound observation apparatus that can prevent lower electrodes of adjacent ultrasound transducers from coming into contact with each other at a joint of respective end portions of a rounded sheet.

Second Embodiment

Figure 5:
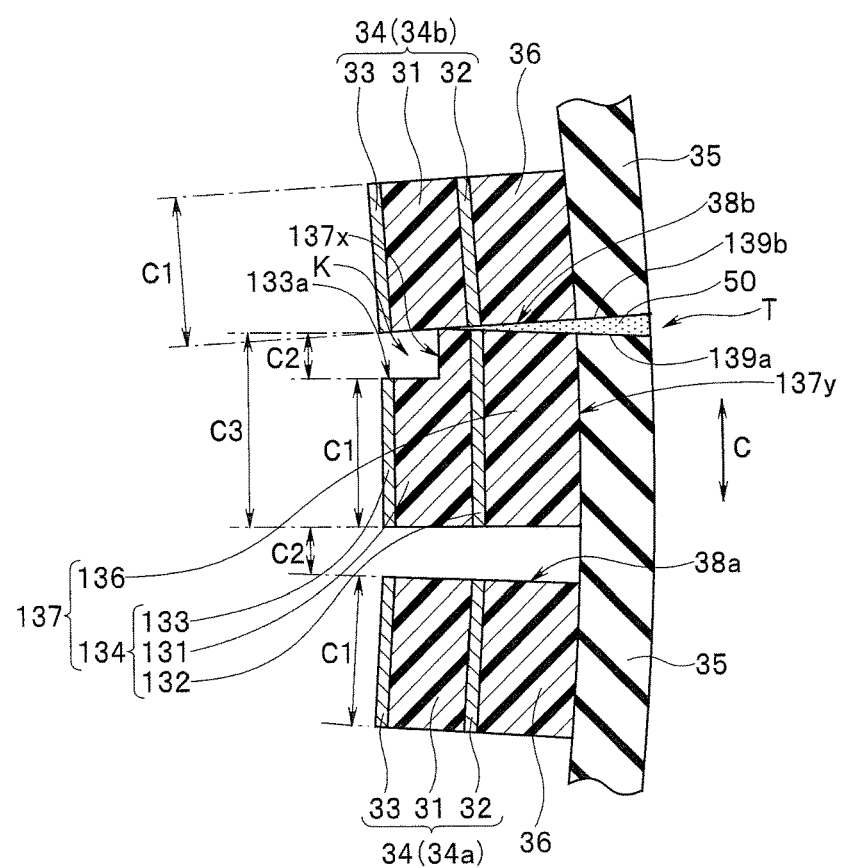
FIG. 5 is a partial cross-sectional view near a joint in a sheet of an ultrasound observation apparatus of a second embodiment.
Figure 6:
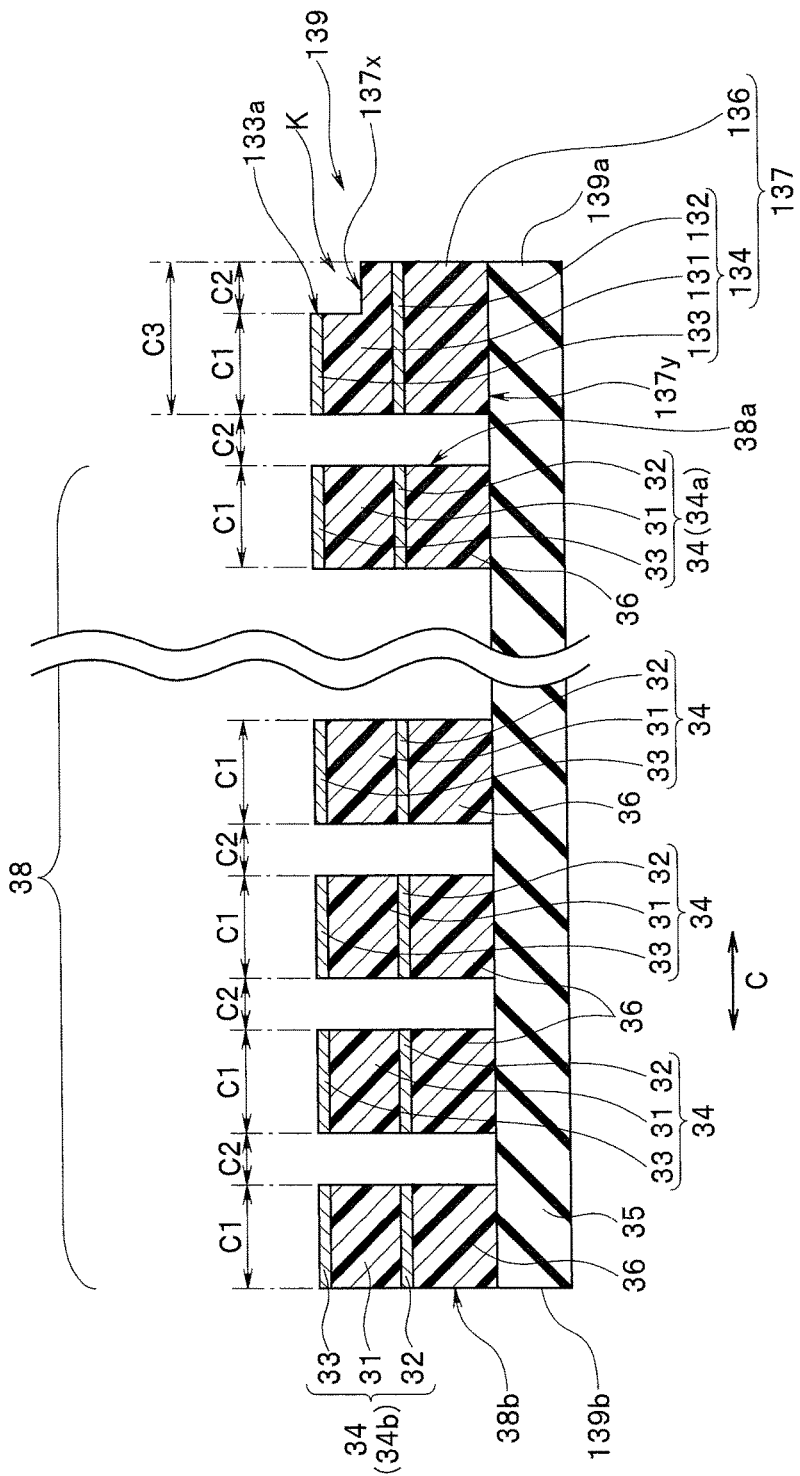
FIG. 6 is a cross-sectional view illustrated by removing the bonding portion from the ultrasound observation apparatus of FIG. 5 and developing the entire sheet.

FIG. 5 is a partial cross-sectional view near the joint in a sheet of an ultrasound observation apparatus of the present embodiment. FIG. 6 is a cross-sectional view illustrated by removing the bonding portion from the ultrasound observation apparatus of FIG. 5 and developing the entire sheet.

Compared to the ultrasound observation apparatus of the first embodiment illustrated in FIGS. 1 to 4, the configuration of the ultrasound observation apparatus of the second embodiment is different in that a columnar portion is configured from at least a second transducer. Therefore, only the difference will be described. The same reference signs are provided to the same components as in the first embodiment, and the description will not be repeated.

As shown in FIG. 6, main parts of a sheet 139 include the plurality of first transducers 34, the first transducer region 38, a columnar portion 137, acoustic matching layers 36 and 136, and the film portion 35 in the present embodiment.

At least a first surface 137x described later of the columnar portion 137 is non-conductive. The columnar portion 137 is disposed, at the predetermined interval C2, adjacent to the first transducer 34a positioned on the first end portion 38a in the arrangement direction C among the plurality of first transducers 34.

The columnar portion 137 has a width of C3 larger than the width C1 by C2 in the arrangement direction C and extends from the one end 39i to the other end 39t in the extension direction H.

More specifically, the columnar portion 137 includes at least the second transducers, each of the second transducers including a second lower electrode 133, a second piezoelectric element 131 disposed on the second lower electrode 133, and a second upper electrode 132 disposed on the second piezoelectric element 131. The second transducers are electronic radial ultrasound transducers with the width of C3 in the arrangement direction C.

Like the first piezoelectric element 31, the second piezoelectric element 131 emits ultrasound toward the second upper electrode 132 along with the vibration and receives a sound wave reflected from the examined site.

The second upper electrode 132 and the second lower electrode 133 are configured to apply a pulse voltage to the second piezoelectric element 131 to vibrate the second piezoelectric element 131. In addition, the second upper electrode 132 configures a GND electrode, and the second lower electrode 133 configures a positive electrode.

As shown in FIG. 5, an end portion 133a in the arrangement direction C of the second lower electrode 133 in the columnar portion 137 is at a position separated by the predetermined distance C2 from the second end portion 38*b* of the first transducer region 38. As a result, part of the second piezoelectric element 131 is exposed, and the first surface 137*x* is configured under the exposed second piezoelectric element 131.

Note that the predetermined distance C2 coincides with the predetermined intervals C2 in the arrangement direction C of the plurality of first transducers 34 in the first transducer region 38.

A dicing blade with the blade width C2 is used to dice the sheet 139 in the second lower electrode 133 closer to an end portion 139*a* in the arrangement direction C along with part of the second piezoelectric element 131, and a cutout K is formed to configure the first surface 137*x* under the second piezoelectric element 131 exposed by the cutout K, the first surface 137*x* having the predetermined distance C2 in the arrangement direction C. For the first surface 137X described above, the second lower electrode 133 may be etched to provide an exposed section K.

Note that the columnar portion 137 may be individually provided only near the one end and the other end in the extension direction H of the sheet 139 in the extension direction H.

The film portion 35 is flexible and connects, in the arrangement direction C, the plurality of first upper electrodes 32 in the first transducer region 38 and a second surface 137*y* facing the first surface 137*x* of the columnar portion 137.

As shown in FIGS. 5 and 6, the present embodiment illustrates an example of a configuration in which the columnar portion 137 includes the acoustic matching layer 136 between the second upper electrode 132 and the film portion 35. However, the arrangement is not limited to this, and the second upper electrode 132 may be directly fixed to the film portion 35.

In a state in which the sheet 139 is rounded such that the film portion 35 becomes the external surface, and the first transducer 34*b* positioned on the second end portion 38*b* and part of the non-conductive first surface 137*x* of the columnar portion 137 are attached to each other as shown in FIG. 5, the bonding portion 50 is configured to bond, in the extension direction H, the columnar portion 137 and the first transducer 34*b* at the joint T between respective end portions 139*a* and 139*b* in the arrangement direction C of the sheet 139.

Note that the bonding portion 50 is also configured from, for example, an adhesive in the present embodiment. The bonding portion 50 may be configured from the same material as the film portion 35.

In the present embodiment, as shown in FIG. 5, the predetermined distance C2 also exists which coincides with the predetermined intervals C2 in the arrangement direction C of the plurality of first transducers 34 in the first transducer region 38 as described above at the joint T where the first transducer 34*b* and part of the non-conductive first surface 137*x* of the columnar portion 137 are attached to each other.

Next, a manufacturing method of the ultrasound observation apparatus 30 configured in this way will be simply described.

First, a step of creating the sheet 139 shown in FIG. 6 is executed. To create the sheet 139, the film portion 35 is formed first. Next, when the acoustic matching layers 36 and 136 are used on the film portion 35, the acoustic matching layers 36 and 136 are formed at the same time.

Next, the first piezoelectric element 31 and the second piezoelectric element 132 provided with the electrodes 32 and 33 and the electrodes 132 and 133 on upper and lower surfaces are bonded on the acoustic matching layer 36 and the acoustic matching layer 136 at the same width as the acoustic matching layer 36 and the acoustic matching layer 136 in the arrangement direction C.

Subsequently, a plurality of grooves with the width C2 in the arrangement direction C are formed on the electrodes 32 and 33, the first piezoelectric element 31, and the acoustic matching layer 36 by using the dicing blade with the blade width C2, for each width C1 in the arrangement direction C.

Furthermore, the dicing blade with the blade width C2 is used for part of the electrode 133 closer to the end portion 139*a* of the sheet 139 and part of the second piezoelectric element 131 to form a groove with the width C2 in the arrangement direction C to thereby form the cutout K. Alternatively, the exposed section K is formed by etching at the etching width C2.

As a result, the sheet 139 is created, in which the plurality of first transducers 34 with the width C1 are arranged on the film portion 35 at the predetermined intervals C2 in the arrangement direction C through the acoustic matching layer 36. The sheet 139 has the predetermined interval C2 between the first transducer 34*a* and the columnar portion 137 in the arrangement direction C and is provided with the cutout K with the predetermined distance C2 between the end portion 133*a* and the end portion 139*a* closer to the end portion 139*a* of the sheet 139 of the columnar portion 137.

Next, a step of rounding the sheet 139 360° is executed as shown in FIG. 5 such that the film portion 35 becomes the external surface, and the first transducer 34*b* positioned on the second end portion 38*b* and part of the first surface 137*x* of the columnar portion 137 are attached to each other.

Lastly, in the state in which the sheet 139 is rounded, a step of bonding by the bonding portion 50 is executed by injecting the bonding portion 50 between the columnar portion 137 and the first transducer 34*b* in the arrangement direction C. As a result, the ultrasound observation apparatus 30 is manufactured.

In this way, the present embodiment has illustrated that the columnar portion 137 in which at least the first surface 137*x* is non-conductive is disposed adjacent to the first transducer 34*a* positioned on the first end portion 38*a* at the predetermined interval C2 in the arrangement direction C among the plurality of first transducers 34 in the first transducer region 38 in the sheet 139 of the ultrasound observation apparatus 30.

The present embodiment has also illustrated that the columnar portion 137 includes the second transducers, each of the second transducers including at least the second lower electrode 133, the second piezoelectric element 131 disposed on the second lower electrode 133, and the second upper electrode 132 disposed on the second piezoelectric element 131.

Furthermore, the present embodiment has illustrated that the dicing blade with the blade width C2 is used to dice the sheet 139 in the second lower electrode 133 closer to the end portion 139*a* along with part of the second piezoelectric element 131 to form the cutout K, or the etching is performed at the etching width C2, and the first surface 137*x* is configured under the second piezoelectric element 131 exposed by the cutout K or the exposed section K, with the predetermined distance C2 in the arrangement direction C.

Note that the present embodiment has illustrated that the predetermined distance C2 coincides with the predetermined interval C2 in the arrangement direction C of the plurality of first transducers 34 in the first transducer region 38.

The present embodiment has also illustrated that the bonding portion 50 bonds, in the extension direction H, the columnar portion 137 and the first transducer 34b in the arrangement direction C at the joint T of the sheet 139 in the state in which the sheet 139 is rounded such that the film portion 35 becomes the external surface, and the first transducer 34b positioned on the second end portion 38b and part of the non-conductive first surface 137x of the columnar portion 137 are attached to each other.

According to this, part of the non-conductive first surface 137x of a second transducer 134 is in contact with the lower electrode 33 of the first transducer 34b at the joint T of the sheet 139, and the lower electrode 33 of the first transducer 34a does not come into contact with the lower electrode 133 of the second transducer 134.

Therefore, the columnar portion 137 can also surely prevent electrical short-circuit at the joint T of the first transducer 34b and the second transducer 134 without separately using the spacer or the like in the present embodiment.

In addition, part of the first surface 137x of the columnar portion 137 is attached to the first transducer 34b, and the bonding portion 50 injected to the joint T does not flow out toward the inner circumference of the sheet 139.

In addition, the cutout K with the predetermined distance C2 is formed on the second transducer 134 in the columnar portion 137. Therefore, the predetermined distance C2 also exists which coincides with the predetermined intervals C2 in the arrangement direction C of the plurality of first transducers 34 in the first transducer region 38 as described above at the joint T where the first transducer 34b and part of the non-conductive first surface 137x of the columnar portion 137 are attached to each other.

As a result, the sheet 139 is provided with a plurality of transducers at equal intervals at the intervals C2 throughout the whole circumference. This can prevent distortion of an ultrasound image of the examined site acquired by the ultrasound observation apparatus 30.

Furthermore, the operator can perform the bonding operation of the joint T just by abutting part of the first surface 137x of the columnar portion 137 to the first transducer 34b and injecting the bonding portion 50 to the joint T, and the operator can simply adjust the position of the predetermined distance C2 in the joint T. Therefore, the bonding operability improves.

In addition, the part of the second transducer 134 configuring the columnar portion 137 excluding the cutout K or the exposed section K in the arrangement direction C also has the width C1 as in the first transducer 34, and the second transducer 134 is separated by the predetermined interval C2 from the first transducer 34a that is the same as the predetermined intervals C2 among the plurality of first transducers 34a. Therefore, the columnar portion 137 can be provided to prevent distortion of an ultrasound image of the examined site acquired by the ultrasound observation apparatus 30.

Note that the other effects are the same as in the first embodiment.

Figure 7:
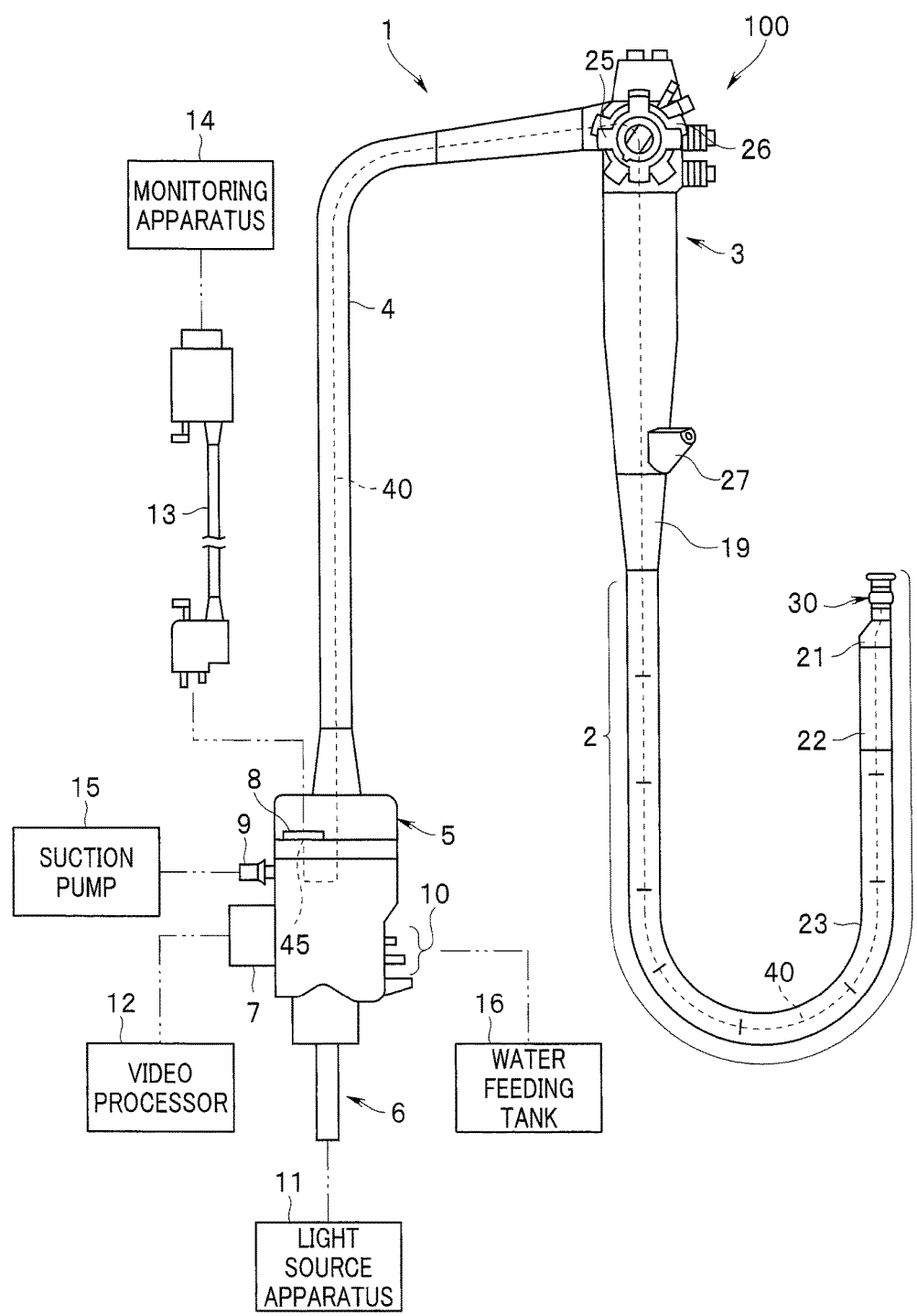
FIG. 7 is a diagram showing an ultrasound endoscope apparatus including the ultrasound observation apparatus of the first and second embodiments.

Hereinafter, an example of a configuration of an ultrasound endoscope apparatus including the ultrasound observation apparatus 30 used in the first and second embodiments will be described with reference to FIG. 7. FIG. 7 is a diagram showing the ultrasound endoscope apparatus including the ultrasound observation apparatus of the first and second embodiments.

As shown in FIG. 7, an ultrasound endoscope apparatus 100 includes an ultrasound endoscope 1, a light source apparatus 11, a video processor 12, a monitoring apparatus 14, a suction pump 15, and a water feeding tank 16.

Main parts of the ultrasound endoscope 1 include an elongated insertion portion 2, an operation portion 3, a flexible universal cord 4 extended from the operation portion 3, and an endoscope connector 5 provided on an extension end of the universal cord 4.

The endoscope connector 5 is provided with a light source connector 6, an electrical connector 7, an ultrasound connector 8, a suction pipe sleeve 9, and an air/water feeding pipe sleeve 10.

The light source apparatus 11 configured to supply illumination light into a subject through a light guide not shown can be attached to and detached from the light source connector 6.

In addition, the video processor 12 configured to execute various types signal processing and the like through an image guide or a signal cable not shown can be attached to and detached from the electrical connector 7.

Furthermore, a connector 45 provided on a proximal end side of an ultrasound transducer cable 40 extending from the transducers 34 and 134 in the ultrasound observation apparatus 30 is electrically connected to the ultrasound connector 8, and the monitoring apparatus 14 can be attached to and detached from the ultrasound connector 8 through an ultrasound cable 13.

In addition, the suction pipe sleeve 9 is provided on an opening of the other end of a treatment instrument insertion channel not shown, and the suction pump 15 can be attached to and detached from the suction pipe sleeve 9 through a suction tube not shown. Furthermore, the air/water feeding pipe sleeve 10 is connected to a fluid supply conduit not shown, and the water feeding tank 16 can be attached to and detached from the air/water feeding pipe sleeve 10 through an air/water feeding tube not shown.

The monitoring apparatus 14 is configured to perform various operation controls of the ultrasound endoscope 1. For example, the monitoring apparatus 14 controls the drive of the ultrasound transducers or executes operation of generating a video signal by executing signal processing of an electrical signal acquired by controlling the drive of the ultrasound transducers.

Note that the video signal generated by the monitoring apparatus 14 is outputted to a display apparatus not shown. As a result, an ultrasound image is displayed on a screen of the display apparatus that has received the video signal.

The insertion portion 2 of the ultrasound endoscope 1 is continuously provided with, in order from a distal end side: a distal end portion 21; a bending portion 22 bendable in, for example, up and down directions and left and right directions; and a long flexible tube portion 23 with flexibility. Note that the ultrasound observation apparatus 30 is positioned in the distal end portion 21.

Bending operation knobs 25 and 26 for performing bending operation of the bending portion 22 are provided on the operation portion 3. A treatment instrument insertion pipe sleeve 27 for introducing a treatment instrument into the body through the treatment instrument insertion channel is provided on a position of the operation portion 3 closer to the insertion portion 2.

The video processor 12 is configured to apply signal processing to an electrical signal transmitted from an image pickup unit not shown provided in the distal end portion 21 to generate a standard video signal. The video processor 12 is configured to output the video signal to the display apparatus not shown to display an endoscopic observation image on the screen of the display apparatus.

Note that the configuration of the ultrasound endoscope 1 is just an example, and it is obvious that the configuration is not limited to the configuration of FIG. 7.

The ultrasound observation apparatus 30 can also be applied to an apparatus other than the ultrasound endoscope apparatus 100, such as an apparatus including an ultrasound treatment instrument.

Although the first transducers 34 and the second transducers 134 are electronic radial ultrasound transducers in the first and second embodiments, the transducers are not limited to these, and it is obvious that the first and second embodiments can also be applied to C-MUT (capacitive micromachined ultrasonic transducers).

What is claimed is:

1. An ultrasound observation apparatus comprising:
    a sheet including:
        a first transducer including a first upper electrode that is a GND electrode, a first piezoelectric element disposed on the first upper electrode, and a first lower electrode that is arranged in a predetermined arrangement direction on the first piezoelectric element and that is a positive electrode;
        a first transducer region in which the first transducer in plurality are arranged at predetermined intervals;
        a columnar portion in which at least a first surface is non-conductive, the columnar portion disposed adjacent to the first transducer positioned on a first end portion in the arrangement direction in the first transducer region; and
        a film portion that is flexible and that connects at least the first upper electrode in plurality in the first transducer region and a second surface facing the first surface of the columnar portion in the arrangement direction; and
    a bonding portion provided between the first transducer positioned on a second end portion in the arrangement direction among the first transducer in plurality in the first transducer region and the columnar portion and configured to maintain a state in which the sheet is rounded such that the film portion of the sheet becomes an external surface, and the first transducer positioned on the second end portion and the first surface of the columnar portion are attached to each other.

2. The ultrasound observation apparatus according to claim 1, wherein
    the columnar portion is configured of a second transducer including at least a second lower electrode, a second piezoelectric element disposed on the second lower electrode, and a second upper electrode disposed on the second piezoelectric element,
    the second lower electrode is positioned at a predetermined distance from the second end portion to expose part of the second piezoelectric element, and the first surface is configured under the exposed second piezoelectric element.

3. The ultrasound observation apparatus according to claim 2, wherein
    the predetermined distance coincides with the predetermined intervals in the arrangement direction of the first transducer in plurality in the first transducer region.

4. The ultrasound observation apparatus according to claim 1, wherein
    an acoustic matching layer is disposed between the first upper electrode and the film portion.

5. A manufacturing method of an ultrasound observation apparatus, the manufacturing method comprising:
    a step of creating a sheet, the sheet including:
        a first transducer including a first upper electrode that is a GND electrode, a first piezoelectric element disposed on the first upper electrode, and a first lower electrode that is arranged on the first piezoelectric element and that is a positive electrode;
        a first transducer region in which the first transducer in plurality are arranged at predetermined intervals;
        a columnar portion in which at least a first surface is non-conductive, the columnar portion disposed adjacent to the first transducer positioned on a first end portion in an arrangement direction of the first transducer in plurality among the first transducer in plurality in the first transducer region; and
        a film portion that is flexible and that connects at least the first upper electrode in plurality in the first transducer region and a second surface facing the first surface of the columnar portion in the arrangement direction;
    a step of rounding the sheet such that the film portion of the sheet becomes an external surface, and the first transducer positioned on a second end portion in the arrangement direction among the first transducer in plurality in the first transducer region and the first surface of the columnar portion are attached to each other; and
    a step of maintaining, by a bonding portion, the state in which the sheet is rounded in the state in which the columnar portion and the first transducer positioned on the second end portion are attached to each other.

* * * * *